(12) United States Patent
Fisher et al.

(10) Patent No.: US 8,906,421 B2
(45) Date of Patent: Dec. 9, 2014

(54) METHODS OF DISSOLVING BLOOD CLOTS AND THE LIKE

(75) Inventors: John S. Fisher, Belleair, FL (US); Fred Ahari, Clearwater, FL (US); Christopher Jon Perry, Largo, FL (US); Lucjan J. J. Hronowski, Bedford, MA (US)

(73) Assignee: MED-Genesis, LLC, Clearwater, FL (US)

( * ) Notice: Subject to any disclaimer, the term of this patent is extended or adjusted under 35 U.S.C. 154(b) by 109 days.

(21) Appl. No.: 13/529,445

(22) Filed: Jun. 21, 2012

(65) Prior Publication Data

US 2012/0328709 A1 Dec. 27, 2012

Related U.S. Application Data

(60) Provisional application No. 61/499,481, filed on Jun. 21, 2011.

(51) Int. Cl.
| | | |
|---|---|---|
| *A61K 33/00* | (2006.01) | |
| *A61K 31/17* | (2006.01) | |
| *A61K 31/16* | (2006.01) | |
| *A61K 31/155* | (2006.01) | |
| *A61K 33/06* | (2006.01) | |
| *A61P 7/02* | (2006.01) | |
| *A61K 47/18* | (2006.01) | |
| *A61K 31/164* | (2006.01) | |
| *A61K 9/00* | (2006.01) | |
| *A61K 31/198* | (2006.01) | |

(52) U.S. Cl.
CPC ............. *A61K 31/164* (2013.01); *A61K 47/183* (2013.01); *A61K 33/00* (2013.01); *A61K 9/0019* (2013.01); *A61K 31/198* (2013.01); *A61K 31/17* (2013.01)
USPC ........... 424/607; 424/611; 514/588; 514/616; 514/638

(58) Field of Classification Search
None
See application file for complete search history.

(56) References Cited

U.S. PATENT DOCUMENTS

| | | | | |
|---|---|---|---|---|
| 5,756,672 | A * | 5/1998 | Builder et al. | 530/350 |
| 6,001,355 | A * | 12/1999 | Dowdle | 424/94.64 |
| 2010/0035992 | A1 * | 2/2010 | Bhushan et al. | 514/566 |

* cited by examiner

*Primary Examiner* — Robert A Wax
*Assistant Examiner* — Randeep Singh
(74) *Attorney, Agent, or Firm* — Nilay J. Choksi; Smith & Hopen, P.A.

(57) ABSTRACT

The present invention provides an aqueous composition and its use for dissolving blood clots in vivo or in clinical or research samples in vitro, said composition comprising at least one chaotropic agent, at least one chelating agent that complexes iron if the chaotropic agent does not complex iron and at least one surface-active emulsifier, the composition being buffered near pH 7.4. The process of dissolving the clot with the aqueous composition is advantageous because it is simple, inexpensive, rapid and can be applied in a variety of contexts, including basic research and clinical situations.

16 Claims, No Drawings

METHODS OF DISSOLVING BLOOD CLOTS AND THE LIKE

CROSS-REFERENCE TO RELATED APPLICATIONS

This non-provisional application claims priority from U.S. Provisional Application No. 61/499,481 filed on Jun. 21, 2011, entitled "Methods of Dissolving Blood Clots and the Like".

FIELD OF INVENTION

This invention relates to composition of matter and methods for dissolving blood clots in vivo or in clinical or research samples in vitro.

BACKGROUND OF INVENTION

Many drugs have been developed to prevent blood clots from forming. Anti-coagulants, including aspirin, warfarin, and heparin, are widely used for the purpose. There are, however, very few therapies that can break down clots already formed. The process of dissolving a clot is called thrombolysis.

Thrombolytic agents work directly upon the fibrin strands within a clot. Examples include plasma activator agents, which increase plasma activator activity, and plasminogen activators, such as streptokinase, urokinase and tissue plasminogen. All these agents digest clots by increasing the amount of plasmin in the blood. Plasminogen is activated and converted into plasmin by enzymes called plasminogen activators, increasing the level of plasmin available to digest clots.

Streptokinase has been utilized in medicine since the 1960s. The least expensive plasminogen activator, streptokinase has caused negative side effects in some patients, such as immune responses. Urokinase is a naturally-occurring protein in humans, especially in the urine. There is therefore no negative immune response associated with its use. Urokinase therapy is usually administered in small doses in combination with other drugs, because it is difficult to purify and therefore rather expensive.

Tissue plasminogen activator (tPA) is an expensive drug for dissolving blood clots. It is unique because it activates only fibrin-bound plasminogen and thus targets clot sites. tPA in human blood is, however, produced in very small amounts by vascular endothelial cells. Recombinant DNA technology has therefore been utilized to make copies of the gene that encodes human tPA. These genes are then transfected into host cells for production of the corresponding proteins. Chinese hamster ovary cells are often utilized for protein production. Recombinant plasminogen must still be converted to plasmin to be effective. Because the overall process can be lengthy and require a large amount of tPA, which is costly, it is desirable to find alternative methods of dissolving blood clots.

SUMMARY OF INVENTION

The present invention provides a simple and inexpensive aqueous composition and its use for dissolving blood clots and effecting hemostasis at a bleeding point; said composition comprising at least one chaotropic agent, at least one chelating agent that complexes iron if the chaotropic agent does not complex iron, and at least one surface-active emulsifier; the composition being buffered near pH 7.4.

Dissolving the clot with the aqueous composition of the present invention is advantageous because it is simple, rapid and can be applied in a variety of contexts, including basic research and clinical situations. The composition is easier to prepare than recombinant tPA. It is more opaque than tPA, possibly rendering the clot visible by standard imaging methods. The rapid removal of iron in the present invention can lead to more rapid lysing of the clot and/or earlier opening of the vessel.

DETAILED DESCRIPTION OF THE PREFERRED EMBODIMENT

In the following detailed description of preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

In the broadest aspect, the present invention provides the use of an aqueous composition for dissolving blood clots, said composition comprising at least one chaotropic agent, at least one chelating agent that complexes iron if the chaotropic agent does not complex iron, and at least one surface-active emulsifier, wherein said composition is buffered near pH 7.4.

Any chaotropic agent known to those skilled in the art can be used in the composition. Examples include, but are not limited to, potassium thiocyanate, barium thiocyanate, calcium thiocyanate, magnesium thiocyanate, sodium thiocyanate, or some other thiocyanate salt, L-arginine, urea, thiourea, guanidinium chloride, lithium perchlorate, ethylene glycol, sodium chloride or magnesium sulfate. Chaotropic agents change the structure of water in a way that makes it less polar, which effectively salts-in proteins and decreases the strength of hydrophobic interactions. The cations barium, calcium and magnesium will also promote disulfide bond reduction in the presence of a suitable reducing agent.

Any iron chelator known to those skilled in the art can be chosen as the chelating agent. Examples include, but are not limited to, deferoxamine, thiocyanate and EDTA disodium dihydrate. They are known to complex strongly with iron. The deep color of the supernatant that is formed when a clot is treated with these reagents dissolved in a suitable buffer indicates that an iron complex is formed. Stripping iron from hemoglobin in red blood cells may weaken a clot and accelerate dissolution.

Any surface-active emulsifier known to those skilled in the art can be selected from among various detergents and ionic surfactants. Examples include, but are not limited to, Polyoxyethylene (20) Sorbitan Monolaurate, Polyoxyethylene (20) Sorbitan Monooleate, polyoxyethylene octylphenyl ether, octanoyl-N-methylglucamide, nanaolyl-N-methylglucamide, decanoyl-N-methylglucamide, sodium lauryl sulfate, deoxycholic acid sodium salt, lithium dodecyl sulfate and sodium lauryl sarcosine. The purpose of this agent is to increase the solubility of otherwise water-insoluble material. The agent may also lower the surface tension of the aqueous composition, thereby facilitating agent clot penetration and clot dissolution.

The buffer is chosen by one skilled in the art from among those that have significant buffering capacity at pH 7.4. Examples include, but are not limited to, phosphate-buffered saline (PBS), ACES, PIPES sodium salt, MOPSO free acid, MOPSO sodium salt, imidazole, MOPS, MOPS sodium salt, TES disodium salt, HEPES free acid, HEPES sodium salt, DIPSO, HEPPSO free acid, POPSO free acid, POPSO disodium salt, HEPPS, tricine buffer and tris. Any conjugate acid/base pair that buffers at pH 7.4 can be used as a buffering agent. pH determines the ionization state of any ionizable groups that may be present, and therefore the solubility, reactivity, surface charge and tertiary structure/function of proteins on which the ionizable groups are found. Different buffer species could contribute meaningfully to parallel clot dissolution mechanisms.

In a preferred embodiment, biocompatible buffers are utilized to dissolve blood clots in a living subject. 'Biocompatible' means the quality of not having toxic or injurious effects on biological systems. Many such buffers are known in the art, for example, PBS.

The invention can be used to dissolve blood clots inside or outside the body. When used inside the body, the aqueous composition can be administered IV for arterial and/or venous clots, IV directly into a clot through a catheter, or IV directly into a venous clot or into a fluid collection or access to improve drainage of complex fluid collections.

In a specific embodiment of the invention, the aqueous composition comprises potassium phosphate buffer, pH 7.4, potassium thiocyanate as the chelating agent and chaotropic agent, and polyoxyethylene (20) sorbitan monooleate as the surface-active emulsifier. The density of the aqueous composition is about 1.07 g/mL. The density of polyoxyethylene (20) sorbitan monooleate is about 1.064 g/mL.

In another specific embodiment of the invention, L-arginine is used as the chaotropic agent.

EXAMPLE

Fresh blood is drawn from a patient by a medical syringe without anti-coagulant pretreatment. A blood clot will form immediately after drawing. The syringe is then cut into several pieces for testing.

The composition of the blood clot-dissolving solution comprises 0.01 M potassium phosphate buffer, pH 7.4, 1.6 M potassium thiocyanate (about 14.5% w/w) and 0.01% v/v polyoxyethylene (20) sorbitan monooleate (about 0.01% w/w).

The blood clot-dissolving solution is added to the blood clot samples at ambient temperature. The blood clots dissolve completely to yield deep red and purple solutions free of turbidity.

The advantages set forth above, and those made apparent from the foregoing description, are thus efficiently attained. Further, since certain changes may be made in the above construction without departing from the scope of the invention, it is intended that all matters contained in the foregoing description or shown in the accompanying drawings shall be interpreted as illustrative and not as limiting.

It is also to be understood that the following claims are intended to cover all of the generic and specific features of the invention herein described, and all statements of the scope of the invention which, as a matter of language, might be said to fall there between.

What is claimed is:

1. An aqueous composition for dissolving blood clots or affecting hemostasis of a bleeding point, comprising:
    a chaotropic agent comprising potassium thiocyanate;
    a surface-active emulsifier comprising polyoxyethylene (20) sorbitan monooleate; and
    a buffering salt comprising potassium phosphate, said buffering salt having an ionization constant near pH 7.4, wherein a clot-dissolving effective amount of tissue plasminogen activator is absent from the composition.

2. The composition of claim 1, wherein the surface active emulsifier comprises an amount of about 0.005% to about 1% by weight.

3. The composition of claim 1, wherein the chaotropic agent comprises an amount of about 5% to about 25% by weight.

4. The composition of claim 1, further comprising a chelating agent that complexes iron, whereby the chelating agent complexes iron if the chaotropic agent does not complex iron.

5. The composition of claim 4, wherein the chaotropic agent comprises potassium thiocyanate.

6. The composition of claim 4, wherein the chelating agent is a deferoxamine.

7. The composition of claim 4, wherein the chelating agent is a thiocyanate.

8. The composition of claim 4, wherein the chelating agent is EDTA disodium dehydrate.

9. The composition of claim 4, wherein the chelating agent comprises an amount of about 0.1% to about 10% by weight.

10. A method of dissolving a blood clot or affecting hemostasis of a bleeding point, comprising applying an aqueous composition to the blood clot or bleeding point, said aqueous composition comprising:
    a chaotropic agent comprising potassium thiocyanate;
    a surface-active emulsifier comprising polyoxyethylene (20) sorbitan monooleate; and
    a buffering salt comprising potassium phosphate, said buffering salt having an ionization constant near pH 7.4, wherein a clot-dissolving effective amount of tissue plasminogen activator is absent from the composition.

11. The method of claim 10, wherein the composition is directly injected into a living subject.

12. The method of claim 11, wherein applying the composition is directly injected to the living subject by administered IV.

13. The method of claim 11, wherein the living subject is a human.

14. The method of claim 10, wherein the blood clot is a clinical sample.

15. The method of claim 10, wherein the blood clot is an arterial and/or a venous clot.

16. The method of claim 10, further comprising a chelating agent that complexes iron, whereby the chelating agent complexes iron if the chaotropic agent does not complex iron.

* * * * *